(12) United States Patent
Henriksen et al.

(10) Patent No.: US 11,335,473 B2
(45) Date of Patent: May 17, 2022

(54) METHOD OF PRODUCING RADIONUCLIDES AND APPARATUS THEREFORE

(71) Applicant: UNIVERSITETET I OSLO, Oslo (NO)

(72) Inventors: Gjermund Henriksen, Mjondalen (NO); Jan Chr. Müller, Hvalstad (NO); Sunniva Siem, Jar (NO); Andreas Görgen, Jar (NO); Bent Wilhelm Schoultz, As (NO)

(73) Assignee: UNIVERSITETET I OSLO, Oslo (NO)

( * ) Notice: Subject to any disclaimer, the term of this patent is extended or adjusted under 35 U.S.C. 154(b) by 449 days.

(21) Appl. No.: 16/315,268

(22) PCT Filed: Jul. 10, 2017

(86) PCT No.: PCT/EP2017/067234
§ 371 (c)(1),
(2) Date: Jan. 4, 2019

(87) PCT Pub. No.: WO2018/007643
PCT Pub. Date: Jan. 11, 2018

(65) Prior Publication Data
US 2019/0311819 A1   Oct. 10, 2019

(30) Foreign Application Priority Data
Jul. 8, 2016   (GB) .................................... 1611925

(51) Int. Cl.
*G21G 1/10*   (2006.01)
*G21G 4/08*   (2006.01)
(Continued)

(52) U.S. Cl.
CPC ................ *G21G 1/10* (2013.01); *G21G 4/08* (2013.01); *G21K 5/08* (2013.01); *A61K 51/025* (2013.01);
(Continued)

(58) Field of Classification Search
CPC .... G21G 1/10; G21G 4/08; G21G 2001/0094; H05H 6/00; G21K 5/08; A61K 51/025
(Continued)

(56) References Cited

U.S. PATENT DOCUMENTS 3,955,093 A * 5/1976 Quinby ................... G21G 1/10
                                                      376/202
4,681,727 A   7/1987 Mirzadeh et al.
(Continued)

FOREIGN PATENT DOCUMENTS

| JP | 2011112413 A | 6/2011 |
|---|---|---|
| JP | 5246881 B2 | 7/2013 |
| WO | 2015195042 A1 | 12/2015 |

OTHER PUBLICATIONS

Sadeghi, "Cyclotron production of 68Ga via proton-induced reaction on 68Zn target", Nukleonika 54 (2009): 25-28. (Year: 2009).*
(Continued)

*Primary Examiner* — Jack W Keith
*Assistant Examiner* — Daniel Wasil
(74) *Attorney, Agent, or Firm* — Eversheds Sutherland (US) LLP (57) ABSTRACT

The present disclosure provides a method and an apparatus for producing astatine-211 from alpha-particle bombardment of bismuth-209. The disclosure also relates to a method and apparatus of producing other radionuclides from target nuclides. The apparatus includes a plate having a recessed portion. The recessed portion has a generally inert surface of ceramic or metal, preferably aluminium oxide that does not
(Continued)

react with molten bismuth. A bismuth target is placed in the recessed portion and held therein by a foil cover. The foil has a melting temperature greater than target nuclide (i.e., for bismuth, >271° C.). The foil and target nuclide are held in the recessed portion by a cover that is fastened over the foil. The cover has an aperture to allow a beam of radiation, such as alpha particles, from a cyclotron or other accelerator to pass through the cover to the foil and target nuclide.

19 Claims, 5 Drawing Sheets (51) Int. Cl.
*G21K 5/08* (2006.01)
*A61K 51/02* (2006.01)
*G21G 1/00* (2006.01)
*H05H 6/00* (2006.01)

(52) U.S. Cl.
CPC ............. *G21G 2001/0084* (2013.01); *G21G 2001/0094* (2013.01); *H05H 6/00* (2013.01)

(58) Field of Classification Search
USPC .................... 376/202, 194, 195, 196, 198
See application file for complete search history.

(56) References Cited

U.S. PATENT DOCUMENTS

| | | |
|---|---|---|
| 5,917,874 A | 6/1999 | Schlyer et al. |
| 2006/0255285 A1* | 11/2006 | Jongen .................. H05H 7/10 250/396 ML |
| 2011/0255646 A1* | 10/2011 | Eriksson ................ G21G 1/10 376/202 |
| 2017/0048962 A1* | 2/2017 | Zeisler .................. G21G 1/10 |

OTHER PUBLICATIONS

Ogawa, "Preparation and evaluation of an astatine-211-labeled sigma receptor ligand for alpha radionuclide therapy", Nuclear medicine and biology 42, No. 11 (2015): 875-879. (Year: 2015).*
Barnhart, "Water-cooled grid support for high-power irradiation with thin target windows", Applied Radiation and Isotopes 58, No. 1 (2003): 21-26. (Year: 2003).*
International Search Report and Written Opinion, PCT/EP2017/067234, dated Oct. 5, 2017 (11 pp.).
GB1611925.7 Search Report, dated Nov. 18, 2016 (7 pp.).
Nagatsu, Kotaro, et al., Production of 211 at by a vertical beam irradiation method, Applied Radiation and Isotopes 94 (2014), pp. 363-371 (9 pp.).

* cited by examiner

METHOD OF PRODUCING RADIONUCLIDES AND APPARATUS THEREFORE

The present disclosure relates to a particle accelerator target for producing radionuclides, particularly a target for the production of astatine-211 in a cyclotron. It also relates to a method of producing radionuclides, such as astatine-211.

BACKGROUND

Astatine-211 ($^{211}$At) is an α-particle emitting radionuclide (alpha-emitter) with a half-life of 7.2 hours. It is highly radiotoxic in its free state. It is an isotope of interest in nuclear medicine, having chemistry similar to iodine.

Approximately 100 α-particle emitting radionuclides are known to exist. However, constraining factors, including physical decay characteristics (half-life, α-particle emission probability, energy and abundance of other emissions, presence of long-lived daughters) as well as other properties, like labelling chemistry and toxicity, limits the number of isotopes that have been evaluated for targeted radiotherapy to about an order of magnitude lower. An additional consideration is the availability of the radionuclide, either as a natural product or from an artificial production source. The majority of α-particle emitting radionuclides that have been investigated extensively for this purpose—$^{212}$Bi, $^{213}$Bi, $^{223}$Ra, $^{224}$Ra, $^{225}$Ac, $^{227}$Th—are products of natural decay chains. The notable exception is $^{211}$At (astatine-211), which requires cyclotron production.

For decades $^{211}$At, even with its relatively short half-life (T½=7.2 hours) and limited availability, has been considered a promising nuclide towards internal radiotherapy because of its combined physical and chemical properties. Today, $^{211}$At-labelled antibodies are being investigated in late clinical trials with promising results, and the nuclear community is searching for production facilities to secure availability and enable more research.

The most efficient production route for $^{211}$At is by the nuclear reaction on natural bismuth with an accelerated alpha particle (i.e. a helium nucleus), $^{209}$Bi(α, 2n)$^{211}$At.

Water cooled targets with open target face of solid bismuth metal are limited by the low melting temperature of bismuth target metal (mp: 271° C.) and the volatility of astatine. In addition, bismuth has among the poorest thermal conduction among all metals. Together, the intrinsic low melting temperature of bismuth and poor heat transfer of the water-cooled target backing puts limits on the target thickness and the applied intensity of beam current in order to prevent loss of product and target metal during cyclotron production.

Existing production targets for $^{211}$At contain bismuth bound to a support backing plate formed by a melting deposition or electrodeposition. Hence, the existing targets contains different amount of bismuth oxides or alloys formed from metals in the attaching support or backing material, depending on the assembling methods used. This target design also puts restrictions on the work-up process of $^{211}$At after production. The most frequent work up method is a dry method using distillation and the second most used method is a wet method using solvation of the bismuth followed by extraction. The size of the target construct adds complexity to the equipment used for work up in addition to product quality and time requirements when processing.

The intrinsic cost for producing $^{211}$At is reasonably modest and comparable to that of commercially available $^{123}$I.

The major inhibition to $^{211}$At availability is the need for a medium-energy (~30 MeV) α-particle beam for its production that is only available from about 30 cyclotrons in the world, in conjunction with low production yield in prior production processes.

The present disclosure aims to improve production rates of astatine-211. The present disclosure is also applicable to the production of other radionuclides.

SUMMARY

According to a first aspect, the disclosure provides a method of producing radionuclides, the method comprising: providing a plate having a recessed portion, wherein the recessed portion has a surface of ceramic or metal; placing a target nuclide in the recessed portion; covering the target nuclide with a foil such that the target nuclide is encapsulated by the foil and the surface of the recessed portion, securing the foil to the plate such that the target nuclide is fixed relative to the plate; wherein the foil has a higher melting temperature than target nuclide; irradiating the encapsulated target nuclide with a beam of radiation.

The target nuclide may be bismuth-209, the radionuclide may be astatine-211, and the beam of radiation may be a beam of alpha particles.

The target nuclide may be zinc-68, the radionuclide may be gallium-68, and the beam of radiation may be a beam of protons.

The foil may have a melting temperature above 1000° C. when the target nuclide has a melting temperature below 1000° C.

The foil may be a cobalt-containing foil, preferably Havar™ foil that is an alloy consisting of 42.5%-no. Co, 20%-no. Cr 13%-no., Ni and the balance Fe, W, Mo, Mn, plus impurities.

The piece of target nuclide may be a generally planar piece of the target nuclide dimensioned to sit in the recessed portion, preferably wherein a thickness of the generally planar piece of target nuclide is between 0.05 mm and 0.5 mm and a largest dimension of the generally planar piece of target nuclide is between 0.5 cm and 3 cm.

The plate may be a plate comprising aluminium.

The encapsulated target nuclide may be held fixed relative to the plate by a cover, the cover having an aperture.

The aperture may be sized to be larger than a beam diameter of the beam of radiation for irradiating the encapsulated target nuclide.

The beam of radiation may be a beam of alpha particles having a beam current greater than 50 μA, preferably the beam current is greater than 1 mA.

The target nuclide may be comprised of one or more of the following: bismuth, a plurality of pieces of bismuth, bismuth oxide, bismuth salt, or powdered bismuth.

According to a second aspect, the present invention provides an apparatus for producing a radionuclide from a horizontally-oriented beam of radiation, the apparatus comprising: a plate having a recessed portion wherein the recessed portion has a surface of ceramic or metal; a target nuclide; and a foil; wherein the target nuclide is sized so as to be encapsulated by the foil and the surface of the recessed portion; wherein the foil has a melting temperature greater than the melting temperature of the target nuclide; the apparatus further comprising means for securing the foil and, thereby, the target nuclide relative to the plate.

The foil may be a cobalt-based alloy foil, preferably wherein the foil comprises an alloy consisting of 42.5%-no., Co, 20%-no., Cr 13%-no., Ni and the balance Fe, W, Mo, Mn, plus impurities.

The foil may have an average thickness of from 4 μm to 500 μm.

The target nuclide may be a generally planar piece of target nuclide dimensioned to sit in the recessed portion or the target nuclide may be electrodeposited onto the plate or onto a coin dimensioned to sit in the recessed portion.

The target nuclide may be comprised of one or more of the following: bismuth, a plurality of pieces of bismuth, bismuth salt, bismuth oxide, or powdered bismuth.

The new target disclosed herein can be dimensioned for internal as well as external targets for the highest available cyclotron currents. When the target nuclide is bismuth-209, this provides highly efficient $^{211}$At production. With the new target, $^{211}$At may be more readily available for research into selective agents for internal radiotherapy of cancer and improve the prospects for industrial production of future $^{211}$At therapy products.

The sealed target design allows melting of the bismuth target and zero-loss production. It is expected that there will be an increase in production yield that is proportional with beam intensity. Known systems for production of astatine-211 utilise beam intensities equal to or lower than 45 μA. This target disclosed herein allows for beam intensities in the mA-range, and, hence, large-scale astatine-211 production.

The apparatus disclosed herein are not limited to the production of astatine-211 from bismuth-209. Rather, the apparatus may be used to hold various different targets for the production of other radionuclides. Further, the target may be suitable for use with other types of particle accelerator, not only cyclotrons. For example, the apparatus may be used in the production of gallium-68 or gallium-66 from zinc targets. One reaction may be the reaction $^{68}$Zn(p, n)$^{68}$Ga. In this reaction, a beam of protons is used instead of an alpha particle beam.

DESCRIPTION OF THE FIGURES

Certain embodiments of the present disclosure will now be described in greater detail by way of example only and with reference to the accompanying drawings in which.

DETAILED DESCRIPTION

Figure 1:
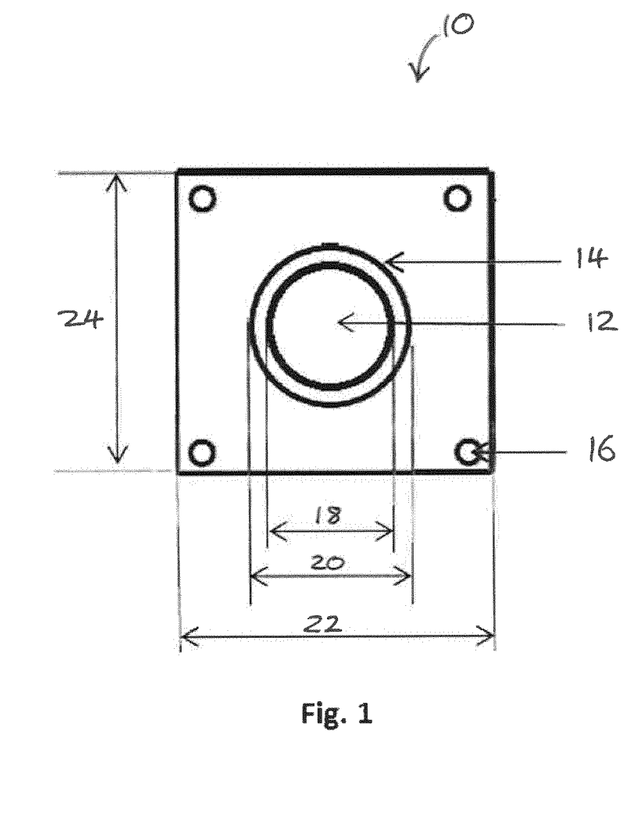
FIG. 1 shows a plan view of a cover having an aperture.

FIG. 1 shows a cover 10 having an aperture 12. The aperture is preferably located in the center of the cover 10. The cover 10 may be made of metal. Preferably, the metal is aluminium such that the external surface of the cover 10 is coated by a layer of aluminium oxide. As described in greater detail below, aluminium is chosen because of its inert oxide surface. Molten bismuth (at temperatures of <300° C.) will only bond with aluminium after physical manipulation that removes the oxide layer, such as scratching. Further planned experiments will provide information for selection of other materials e.g. copper, silver, etc. for the plate 30 and cover 10.

The cover 10 of FIG. 1 may be approximately square (i.e. length 24=length 22 in FIG. 1) and have an assembly hole 16 in each corner. These assembly holes 16 are for receiving fasteners 15, such as screws or pins, to hold the cover 10 to a plate 30 that is shown in FIG. 2.

Figure 2:
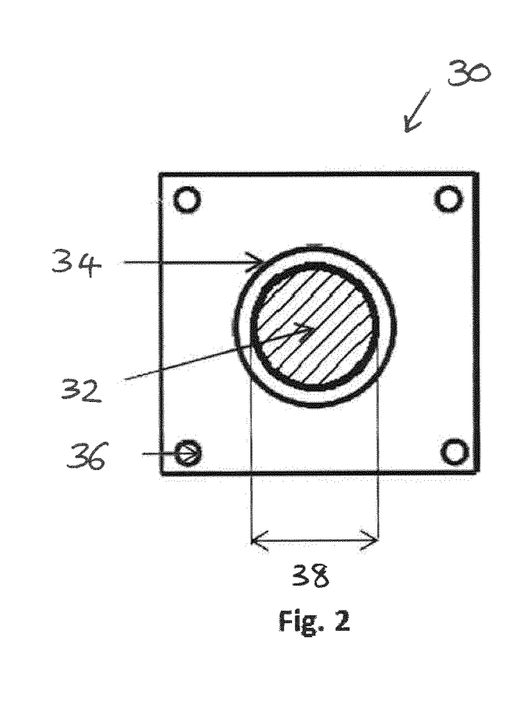
FIG. 2 shows a plan view of a plate having a recessed portion.
Figure 3:
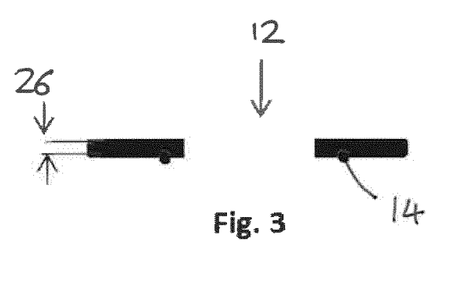
FIG. 3 shows a side view of the cover of FIG. 1.

The plate 30, as shown in FIG. 2, may be approximately square and have an assembly hole 36 in each corner for joining the cover 10 to the plate 30. The assembly holes 15 of the cover 10 should align with the assembly holes 36 on the plate 30 when the cover 10 is laid on top of the plate 30. The plate is preferably made of aluminium such that the external surface of the plate is coated by a layer of aluminium oxide.

Figure 4:
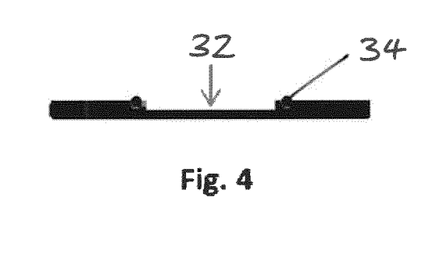
FIG. 4 shows a side view of the plate of FIG. 2.

As shown in FIG. 4, the plate 30 may have a recessed portion 32 in the center such that a center of the recessed portion 32 is coaxial with a center of the aperture 12 of the cover 10 when the cover 10 is attached to the plate 30. In one embodiment, the recessed portion 32 is circular and the aperture 12 is circular. In this embodiment, the recessed portion 32 may have a larger diameter 38 than the diameter 18 of aperture 12. Alternatively, the diameter 38 of the recessed portion 32 may be equal to or smaller than the diameter 18 of the aperture 12. The recessed portion 32 does not extend through the entire thickness 26 of the plate 30. That is, the recessed portion 32 may take the form of a blind hole in the plate 30.

Alternatively, the plate 30 and/or the recessed portion 32 may be made from other materials. It is envisaged that many ceramic materials are suitable. Further, the plate 30 and/or recessed portion 32 may be formed from metals that are inert in the presence of the target nuclide (at, at least, the melting temperature of the target nuclide) and the produced radionuclide. For example, silver, gold, or copper may be suitably inert for the production of astatine-211 or other radionuclides.

The recessed portion may a surface of aluminium oxide. As described in detail below, bismuth is placed in the recessed portion 32 in contact with the aluminium oxide surface.

A sealing ring 14, such as an O-ring, may be disposed in the cover 10. A sealing ring 34, such as an O-ring, may be disposed in the plate 30. Preferably, the two sealing rings 14, 34, are of equal size and are located so as to be coaxial when the cover is laid on top of the plate and fastened thereto. The sealing rings 14, 34 are to assist with gripping and sealing when the cover 10 is fastened to the plate 30.

The sealing ring 14, 34 may be rubber. Alternatively, the sealing rings 14, 34 may be any other material that is inert, heat-resistant (to the degree of the target temperature), and sufficiently compressible/sealable to prevent gas leakage when the sealing rings 14, 34 are compressed pressed when the cover 10 is fastened to the plate 30.

Figure 5:
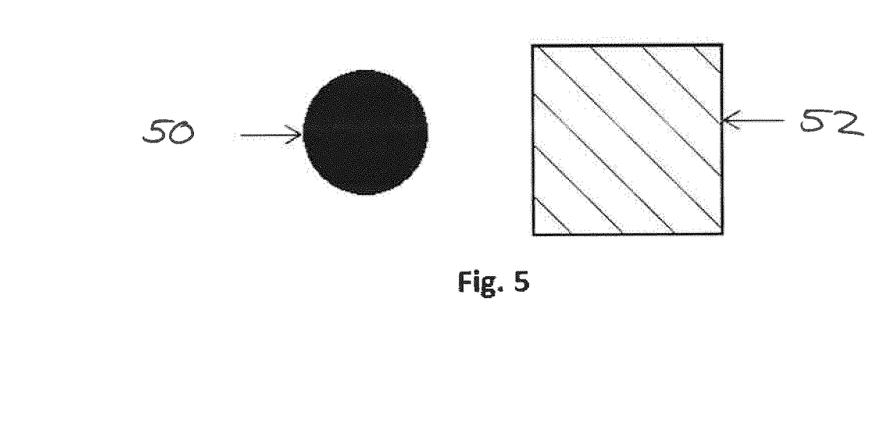
FIG. 5 shows a piece of bismuth and a piece of foil.
Figure 6:
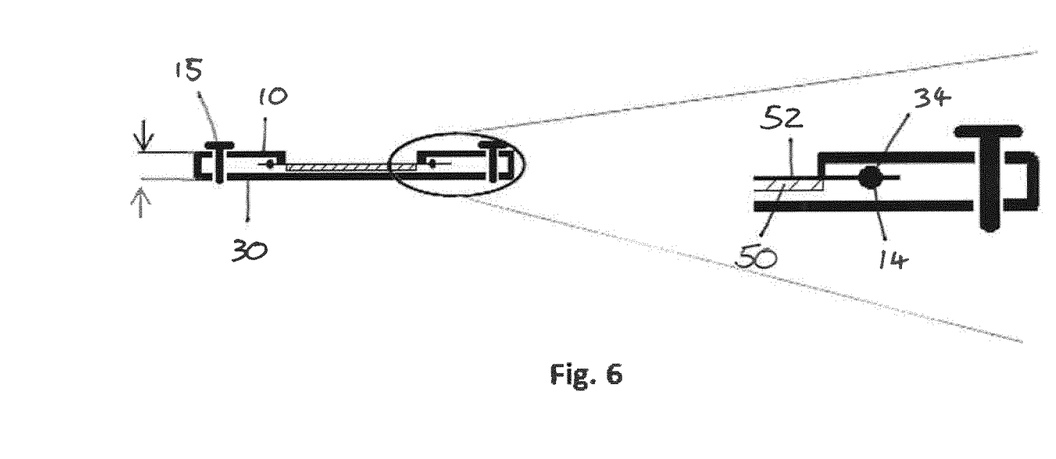
FIG. 6 shows a side view and enlarged side view of the apparatus formed from the cover, plate, target nuclide, and foil.
Figure 7:
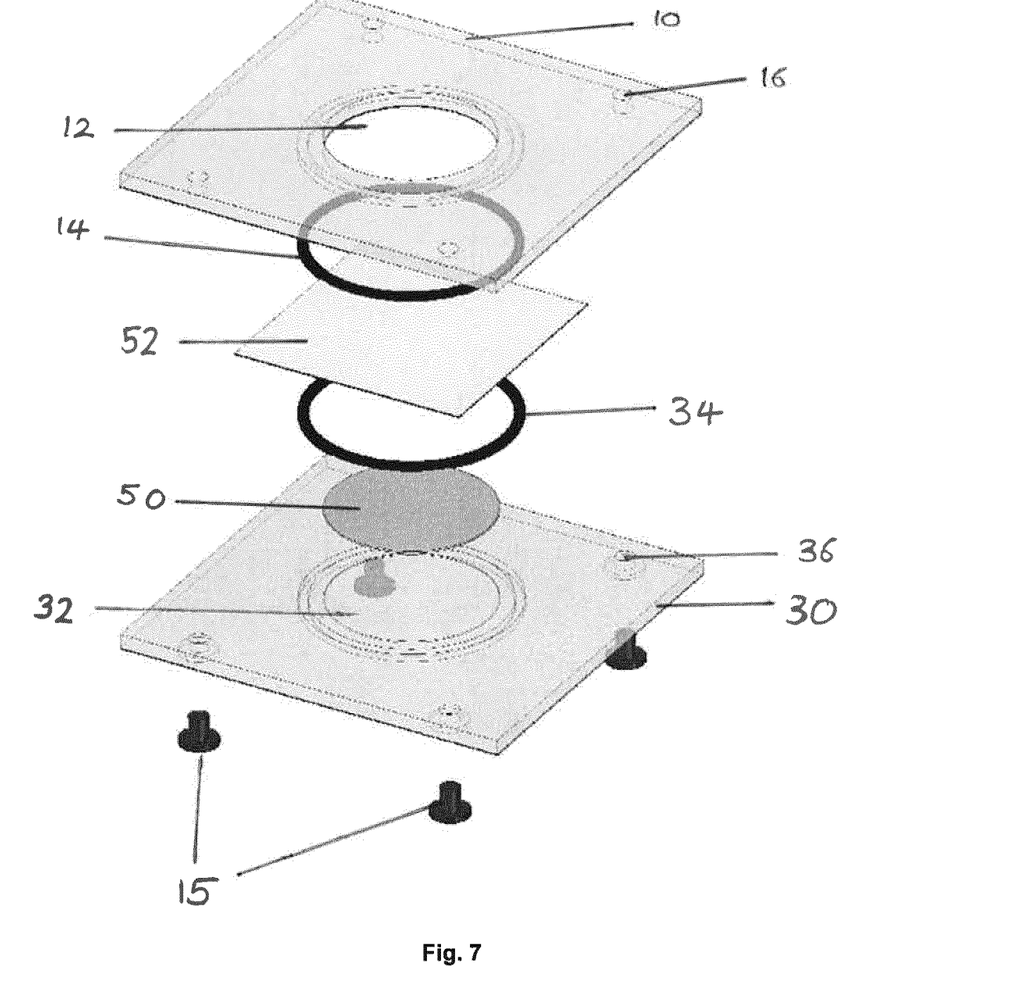
FIG. 7 shows an exploded view of the apparatus formed from the cover, sealing rings, plate, foil, and target nuclide

A target nuclide 50 may be placed in the recessed portion 32. The target nuclide 50 is described hereafter as a piece of bismuth 50, but other target nuclides are possible. As shown in FIG. 5, the piece of bismuth 50 may take the shape of a coin having a diameter less than or equal to the diameter 38 of the recessed portion 32. Other shapes are also envisaged for the piece of bismuth 50. Further, multiple pieces of bismuth 50, bismuth oxides, bismuth salts, or powdered bismuth may be used instead of a unitary piece of bismuth 50. Preferably the bismuth 50 is shaped to match the shape of the recessed portion 32.

Other target nuclides may be used for the production of other radionuclides. For example, instead of bismuth-209, there may be provided zinc-68 for the production of gallium-68. This reaction may require protons (p, n) to be accelerated into the zinc-68 to produce the gallium-68. By contrast, to produce astatine-211, bismuth-209 is bombarded with alpha particles (α, 2n). Similar to bismuth-209, the other target nuclides may be provided in other forms such as salts or oxides, and maybe provided as single unitary pieces, isotope enriched or natural isotopes. The target material may be deposited, e.g. electrodeposited, such as onto an insertable coin sized to fit in the recessed portion, or as multiple pieces, or in powdered form.

After bismuth 50 has been placed in the recessed portion 32 of the plate 30, a foil 52 may be laid on top of the bismuth 50. The foil 52 may have a melting temperature above that of bismuth (i.e. above 271° C.) and is preferably made of a material that will not react with the bismuth 50. Preferably, the foil will not interact, or only interact minimally, with the beam of alpha particles that will be used to convert the bismuth to astatine-211. For example, the foil 52 may be a cobalt alloy foil. One suitable cobalt alloy foil is the commercially-available Havar™ foil 52, which is composed of 42.5%-no. Co, 20%-no. Cr, 13%-no. Ni, and the balance Fe, W, Mo, Mn, plus impurities. This foil 52 has a melting temperature of 1480° C. and an average thickness of 10 μm. Other suitable materials may be used for the foil 52, for example, aluminium foil may be suitable. Further, different thicknesses of foil may be used. The foil will reduce the energy of the incoming alpha particle beam (described in greater detail below). Thus, one criterion governing the choice of foil material and thickness is based on the energy of the particle beam. Optimal production rates of astatine-211 may be achieved with the alpha particle beam impacting the bismuth-209 (i.e. after passing the foil) having an optimal energy of 28.5 MeV. This reduces the production of (unwanted) astatine-210. The above-mentioned Havar™ foil reduces beam energy by 1.2 MeV. Aluminum foil is expected to have only 40% of the stopping power of Havar™. Preferably, the foil material will have a combination of low stopping power as well as being chemically inert and physically stable in the presence of heated target material (e.g. molten bismuth).

The foil 52 may be dimensioned such that it may be overlaid on the sealing rings 14, 34 of the plate 30 and touch the sealing rings at every point. That is, the foil 52 may be larger than the sealing ring border. For example, the foil shown in FIG. 5 is square and has a side-length greater than diameter 20 of the sealing rings 14, 34 shown in FIGS. 1-4. Preferably, the sealing rings are sufficiently compressible such that, when the cover 10 is fastened to the plate 30, the foil 52 is contacted and held by both the cover 10 and the plate 30.

Alternatively, the foil 52 may be provided integrally with the cover 10. In this embodiment, the aperture 12 consists of a thin portion of the cover, either made from the same material as the cover 10 or from a separate material joined to the cover. This thin portion of the cover 10 is thin so as to limit the energy loss of radiation passing through the aperture, so that radiation may interact with the target nuclide held in the recessed portion, beneath the thin portion that is the aperture 12 of the cover 10.

During assembly, the bismuth 50 may be placed in the recessed portion 32. The foil 52 may then be laid on top of the bismuth 50. The cover 10 may then be placed on top of the plate 30 and the foil 52, such that the sealing ring 14 of the cover 10 presses the foil 52 into the sealing ring 34 of the plate 30. The cover 10 may then be fastened to the plate 30.

Pressure from the cover 10 onto the foil 52, and from the foil 52 onto the bismuth 50 may hold the bismuth 50 in place within the recessed portion 32 of the plate 30. The entire assembly may then be spatially oriented and the bismuth 50 will stay in place within the recess. That is, the bismuth is encapsulated in a region defined by the foil and the recessed portion. If the bismuth 50 extends above the depth of the recessed portion 32, then a portion of the plate between the recessed portion 34 and the sealing ring 34 may also form part of the encapsulating region. For example, the plate 30 may be oriented vertically such that the normal line from the base of the recessed portion 32 points horizontally. This allows the apparatus to be used with a horizontally oriented beam of alpha-particles from a cyclotron. Alternatively, the plate 30 may be laid flat such that the normal line from the base of the recessed portion 32 points vertically up or down. This allows the apparatus to be used with a vertically oriented beam of alpha-particles from a cyclotron. That is, the target may be used in any spatial orientation which may increase the number of suitable cyclotrons the target may be used with.

Production of Astatine-211 or Other Radionuclides

The apparatus may be presented as a target at the output of a cyclotron or other particle accelerator. Hereafter, the disclosure will refer to cyclotrons, but it is to be understood that the invention is not so limited and other particle accelerators may be used as appropriate. The cyclotron may produce a beam of accelerate a-particles and this may be aimed at the bismuth 50 held by the apparatus.

Astatine-211 may be produced by bombarding bismuth-209 (the primary naturally-occurring isotope of bismuth) with a-particles having energies of ~28-30 MeV, preferably 28.5 MeV to mimimise production of astatine-210. Different target nuclides will have different particle types (e.g. alpha particles, deuterium ions etc.) for the radiation beam and different preferred particle energies.

Cyclotrons for accelerating α-particles typically produce a beam of particles that has a beam diameter of the order of 1 cm at the target location. In the present apparatus, the aperture 12 may be chosen to have a larger diameter than the particle beam of the cyclotron. In this preferred arrangement, the particle beam exiting the cyclotron is incident on the foil 52 first and then the bismuth 50, without the material of the cover 10 being in the path of the particle beam.

The effective thickness of bismuth under α-particle bombardment to produce astatine-211 (i.e. at the preferred energies) is between 100-200 μm. That is, reactions between alpha-particles and bismuth atoms are expected to occur primarily within the first 200 μm depth of the piece of bismuth 50. Other target nuclides and other radiation beams will have different effective thicknesses.

The bismuth 50 may melt under the particle beam. The foil 52, having a much higher melting temperature than bismuth, may resist melting and thus acts to contain the molten or partially-molten bismuth 50 within the recessed portion 32 as the bismuth 50 is converted into astatine-211. The foil 52 may also prevent any release of bismuth or astatine to the atmosphere. This may be a useful safety feature inherent to the present design, given the known toxicity and radioactivity of astatine-211.

After irradiation by α-particles, the apparatus may be removed from the cyclotron. The foil 52 is preferably selected to be inert with respect to bismuth, molten bismuth and astatine. Further, the foil is preferably selected to be physically stable under the expected heating of the target nuclide. For example, the foil may have a melting temperature higher than, preferably much higher than, the melting temperature of the target nuclide. In this case, the irradiated bismuth/astatine mix, after resolidifying, may be easily separated from both the recessed portion 32 and foil 52.

By way of non-limiting example, the plate 30 and cover 10 may each be 40×40 mm and the aperture 12 of the cover 10 may have a diameter 18 of 10-20 mm, preferably 17 mm. The recessed portion may have a diameter 38 of 20-22 mm and 0.15 mm in depth. The piece of bismuth 50 may be a cylinder having a diameter of 17 mm and a thickness of 0.2 mm. The foil 52 may be 25×25 mm and 0.01 mm thick. Thus, when the piece of bismuth 50 is placed in the recessed portion 32, it extends above the rim of the recess by 0.05 mm and the foil 52 thickness adds an extra 0.01 mm. When the cover 10 is fastened to the plate 30, the bismuth 50 is firmly held in the recessed portion 32 by pressure from the cover 10 holding the foil 52 against the plate 30.

As a distinction from prior art methods and apparatus, the target metal piece may be unbound and free, as a piece resting on the plate 30. This allows use of pure target metal (bismuth) that promotes simpler production equipment, faster handling, and improved product quality. After solidifying, the target metal should not have bonded to the target holder and can be worked up separately providing simpler and faster workup procedure of the produced astatine-211.

The present disclosure seeks to improve upon the prior art. A sealed-target concept is presented in "*Production of $^{211}At$ by a vertical beam irradiation method*" by Kotaro Nagatsu et. al. *Applied Radiation and Isotopes* 94 (2014) 363-371.

This document presents an astatine-211 production target that allows the bismuth metal to melt during the production of astatine-211. The researchers' major purpose with the design was to simplify target preparation, for example, to avoid plating of bismuth onto backing plates (i.e. onto the target holder). These researchers solved this by dropping shots of bismuth into a target capsule. Their design requires the target to be placed under a vertically-oriented particle beam, directed from above, to keep the molten bismuth surface at 90 degrees with respect to the incoming beam. To prevent loss of the astatine-211 product and bismuth target, the capsule is covered with cooled aluminium foils. It is reported that this setup results in about 6 MeV in energy loss between particles leaving the accelerator and particles reaching the bismuth. Further, the foil design only provides a semi-sealed target and does not provide the same safety as the completely sealed design disclosed herein.

The present disclosure may offer the following advantages over this known production method. The published cyclotron target is designed for a vertical beam only. This excludes use of that device inside a cyclotron where the beam is horizontal.
By contrast, the present design allows astatine-production from both vertical and horizontal beams.
is designed with an entrance foil that requires cooling that was performed by barriers between the target and cyclotron that cause energy reduction of the particle beam. To reach the necessary 28-29 MeV energy for the production of astatine-211, the known target design cannot be used for cyclotrons with a maximum energy of 30 MeV, which extensively limits the available production facilities worldwide.
By contrast, the presently disclosed design does not require cooling of the entrance foil 52. The preferred entrance foil 52 only reduces the alpha particle energy by 1.2 MeV and thus may be used for astatine-211 production with 30 MeV cyclotrons.
metal melts and binds to the target holder during and after exposure to particle beam.
By contrast, the present design may allow for separation of target metal from target support after beam exposure.
comprises a capsule with a dead volume above the target bismuth of 0.8 ml. This allows astatine product and target metal to redistribute inside the target during production. Only 10% of the product remains in the target metal afterwards due to in situ distillation and redistribution.
By contrast, the present design allows for a very limited dead volume, potentially zero dead volume, because the entrance foil 52 keeps and shapes the bismuth in position within the recessed portion 32 against the production beam. This may prevent the bismuth metal and astatine products from redistributing inside the target holder.
system comprises a cooled entrance foil to which about 30% of the produced astatine gets bonded.
By contrast, The present disclosure may use an entrance foil 52 that faces the cyclotron vacuum directly without cooling and is physically in contact with the bismuth 50 without dead volume. This may prevent temperature gradients (cold spots) that increase undesirable redistribution and enrichment of products inside the target.
requires product work up performed by heating and distillation from the entire bismuth shot with the secondary aluminium foil. The target in the known art is larger than previous published solutions and requires therefore larger processing equipment.
By contrast, the present design may allow for workup from a small, single and pure bismuth metal without pollution from aluminium. It may also provide the possibility of using miniaturized processing equipment and product work up procedures by chemically dissolved targets.

Further, the presently disclosed apparatus may be suitable for much higher particle beam currents than used previously for production of astatine-211. The maximum beam current used in previously published work on astatine-211 production was <45 µA (microamp). The present disclosure may be suitable for beam currents well into the mA (milliamp) range. It is expected that astatine-211 production yields will increase proportionally to particle beam intensity. Thus, the present disclosure may allow for increased production yields and decreased production time for the production of astatine-211 from bismuth-209. Further, the present disclosure may be used with other target nuclides. With suitable choice of foil and plate material for a given setup, the apparatus is suitable for the production of other radionuclides, with in other types of accelerator, and with other types of radiation beam.

The invention claimed is:
1. A method of producing radionuclides, the method comprising:
providing a plate having a recessed portion, wherein the recessed portion has a surface of ceramic or metal;
placing a solid target nuclide in the recessed portion;
covering the target nuclide with a foil such that the target nuclide is encapsulated by the foil and the surface of the recessed portion, such that the target nuclide is entirely surrounded by the foil and the plate, wherein the foil and the plate abut the target nuclide;

releasably securing the foil to the plate such that the target nuclide is fixed to the plate while the foil is secured to the plate and the plate and the foil seal around the target nuclide;

wherein the target nuclide is not bonded to the plate nor to the foil;

wherein the foil has a higher melting temperature than the target nuclide;

irradiating the encapsulated target nuclide with a beam of radiation to produce a radionuclide.

2. The method of claim 1, wherein the target nuclide is bismuth-209, the radionuclide is astatine-211, and the beam of radiation is a beam of alpha particles.

3. The method of claim 1, wherein the target nuclide is zinc-68, the radionuclide is gallium-68, and the beam of radiation is a beam of protons.

4. The method of claim 1, wherein the foil has a melting temperature above 1000° C. and the target nuclide has a melting temperature below 1000° C.

5. The method of claim 1, wherein the foil is a cobalt-containing foil.

6. The method of claim 1, wherein the target nuclide is a planar piece of the target nuclide dimensioned to sit in the recessed portion.

7. The method of claim 6, wherein a thickness of the planar piece of target nuclide is between 0.05 mm and 0.5 mm, and wherein a largest dimension of the planar piece of target nuclide is between 0.5 cm and 3 cm.

8. The method of claim 1, wherein the plate is a plate comprising aluminium.

9. The method of claim 1, wherein the encapsulated target nuclide is further held fixed to the plate by a cover, the cover having an aperture.

10. The method of claim 9 wherein the aperture is sized to be larger than a beam diameter of the beam of radiation for irradiating the encapsulated target nuclide.

11. The method of claim 1, wherein the beam of radiation is a beam of alpha particles having a beam current greater than 50 µA.

12. The method of claim 11, wherein the beam current is greater than 1 mA.

13. The method of claim 1, wherein the target nuclide is comprised of one or more of the following: bismuth, a plurality of pieces of bismuth, bismuth oxide, bismuth salt, or powdered bismuth.

14. Apparatus for producing a radionuclide from a horizontally-oriented beam of radiation, the apparatus comprising:

a plate having a recessed portion wherein the recessed portion has a surface of ceramic or metal;

a solid target nuclide; and a foil;

wherein the solid target nuclide is located in the recessed portion and is sized so as to be encapsulated by the foil and the surface of the recessed portion, and the solid target nuclide is encapsulated by the foil and the surface of the recessed portion, such that the target nuclide is entirely surrounded by the foil and the plate, wherein the foil and the plate abut the target nuclide;

wherein the target nuclide is not bonded to the plate and not bonded to the foil;

wherein the foil has a melting temperature greater than the melting temperature of the target nuclide;

the apparatus further comprising releasable means arranged to secure the foil to the plate such that the foil fixes the target nuclide to the plate in the recessed portion and the plate and the foil seal around the target nuclide.

15. The apparatus of claim 14, wherein the foil is a cobalt-based alloy foil.

16. The apparatus of claim 15, wherein the foil is made of an alloy consisting of 42.5%-no. Co, 20%-no. Cr 13%-no., Ni and the balance Fe, W, Mo, Mn, plus impurities.

17. The apparatus of claim 14, wherein the foil has an average thickness of from 4 µm to 500 µm.

18. The apparatus of claim 14, wherein the target nuclide is a planar piece of target nuclide dimensioned to sit in the recessed portion or wherein the target nuclide is electrodeposited onto the plate or onto a coin dimensioned to sit in the recessed portion.

19. The apparatus of claim 14, wherein the target nuclide is comprised of one or more of the following: bismuth, a plurality of pieces of bismuth, bismuth salt, bismuth oxide, or powdered bismuth.

* * * * *